United States Patent
Woudenberg et al.

(10) Patent No.: US 9,944,806 B2
(45) Date of Patent: *Apr. 17, 2018

(54) URETHANE COMPOUNDS

(71) Applicant: Markem-Imaje Corporation, Keene, NH (US)

(72) Inventors: Richard C. Woudenberg, Keene, NH (US); Michael P. Secord, West Chesterfield, NH (US)

(73) Assignee: Markem-Imaje Corporation, Keene, NH (US)

( * ) Notice: Subject to any disclaimer, the term of this patent is extended or adjusted under 35 U.S.C. 154(b) by 377 days.

This patent is subject to a terminal disclaimer.

(21) Appl. No.: 14/713,683

(22) Filed: May 15, 2015

(65) Prior Publication Data

US 2016/0090492 A1 Mar. 31, 2016

Related U.S. Application Data

(63) Continuation-in-part of application No. 14/497,126, filed on Sep. 25, 2014, now Pat. No. 9,410,051.

(51) Int. Cl.
| | | |
|---|---|---|
| *C09D 11/12* | (2006.01) | |
| *C09D 11/34* | (2014.01) | |
| *C07C 271/12* | (2006.01) | |
| *C07C 275/10* | (2006.01) | |

(52) U.S. Cl.
CPC ............ *C09D 11/12* (2013.01); *C07C 271/12* (2013.01); *C07C 275/10* (2013.01); *C09D 11/34* (2013.01)

(58) Field of Classification Search
CPC ....... C09D 11/12; C09D 11/34; C07C 271/12; C07C 275/10
USPC ..... 106/31.43, 31.29, 31.75, 31.61; 560/157, 560/158
See application file for complete search history.

(56) References Cited

U.S. PATENT DOCUMENTS

| | | | |
|---|---|---|---|
| 4,745,420 A | 5/1988 | Gerstenmaier | |
| 4,951,067 A | 8/1990 | Spehrley | |
| 5,006,170 A | 4/1991 | Schwarz | |
| 5,041,161 A | 8/1991 | Cooke | |
| 4,751,528 A | 10/1991 | Spehrley, Jr. et al. | |
| 5,122,187 A | 6/1992 | Schwarz | |
| 5,514,209 A | 5/1996 | Larson | |
| 5,750,604 A * | 5/1998 | Banning | C09D 11/34 101/491 |
| 5,782,966 A | 7/1998 | Bui | |
| 5,830,942 A | 11/1998 | King | |
| 5,863,319 A | 1/1999 | Baker | |
| 5,891,228 A | 4/1999 | Baker | |
| 5,994,453 A | 11/1999 | Banning | |
| 6,048,925 A | 4/2000 | Titterington | |
| 6,180,692 B1 | 1/2001 | Bridgeman | |
| 6,306,203 B1 | 10/2001 | Malhotra | |
| 6,309,453 B1 * | 10/2001 | Banning | C09D 11/34 106/31.29 |
| 6,329,453 B1 | 12/2001 | Meinhardt | |
| 6,343,850 B1 | 2/2002 | Domagall | |
| 6,410,478 B1 | 6/2002 | Torii | |
| 6,620,228 B1 | 9/2003 | King | |
| 6,702,884 B2 | 3/2004 | Brown | |
| 6,730,150 B1 | 5/2004 | Titterington | |
| 6,860,930 B2 * | 3/2005 | Wu | C09D 11/34 106/31.29 |
| 6,872,243 B2 | 3/2005 | Breton | |
| 6,989,052 B1 | 1/2006 | Wu | |
| 7,064,230 B2 | 6/2006 | Titterington | |
| 7,144,450 B2 | 12/2006 | Goredema | |
| 7,153,349 B2 | 12/2006 | Carlini | |
| 7,220,300 B2 | 5/2007 | Goredema | |
| 7,347,892 B2 | 3/2008 | Bedford | |
| 7,520,222 B2 | 4/2009 | Titterington | |
| 7,541,406 B2 | 6/2009 | Banning | |
| 7,665,835 B2 | 2/2010 | Goredema | |
| 7,810,922 B2 | 10/2010 | Gervasi | |
| 7,874,664 B2 | 1/2011 | Gervasi | |
| 8,152,288 B2 | 4/2012 | Williams | |
| 9,410,051 B2 * | 8/2016 | Benjamin | C09D 11/12 |
| 9,631,108 B2 * | 4/2017 | Secord | C09D 11/12 |
| 2006/0004123 A1 | 1/2006 | Wu | |
| 2006/0035999 A1 | 2/2006 | Bedford | |
| 2006/0117992 A1 | 6/2006 | Goredema | |
| 2006/0117993 A1 | 6/2006 | Carlini | |
| 2006/0122291 A1 | 6/2006 | Goredema | |
| 2007/0123642 A1 | 5/2007 | Banning | |
| 2008/0098929 A1 | 5/2008 | Turek | |
| 2009/0249977 A1 | 10/2009 | Wong | |
| 2010/0018417 A1 | 1/2010 | Gervasi | |
| 2010/0020148 A1 | 1/2010 | Gervasi | |
| 2011/0262711 A1 | 10/2011 | Chopra | |
| 2012/0154479 A1 | 6/2012 | Wu | |
| 2012/0157562 A1 | 6/2012 | Chopra | |
| 2014/0146114 A1 | 5/2014 | Toosi | |

FOREIGN PATENT DOCUMENTS

| | | |
|---|---|---|
| CN | 101191026 A | 6/2008 |
| EP | 479501 B1 | 7/1996 |

(Continued)

OTHER PUBLICATIONS

European Patent Application 15186688.6, European Search Report dated Feb. 15, 2016, 4 pages.

(Continued)

*Primary Examiner* — Helene Klemanski
(74) *Attorney, Agent, or Firm* — Fish & Richardson P.C.

(57) ABSTRACT

This disclosure relates to compounds of formula (I), as well as related ink compositions and printing methods:

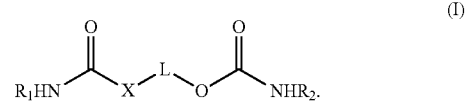

In formula (I), L, X, $R_1$, and $R_2$ are defined in the specification.

27 Claims, No Drawings

(56) References Cited

FOREIGN PATENT DOCUMENTS

| EP | 1099734 | B1 | 5/2008 |
|---|---|---|---|
| EP | 1792959 | B1 | 7/2008 |
| GB | 2065149 | A | 6/1981 |
| WO | WO1994014902 | A1 | 7/1994 |
| WO | WO2008002833 | A | 1/2008 |

OTHER PUBLICATIONS

European Application No. 15 186 690.2, Communication pursuant to Article 94(3) EPC, dated Feb. 23, 2016, 7 pages.
European Patent Application 15186690.2, European Search Report dated Feb. 14, 2016, 4 pages.
Chinese Application No. 201510624398.0, Notification of the First Office Action and Search Report (with English translation), dated Dec. 27, 2017, 15 pages.

* cited by examiner

URETHANE COMPOUNDS

CROSS REFERENCE TO RELATED APPLICATION

This application is a continuation-in-part of U.S. Utility application Ser. No. 14/497,126, filed on Sep. 25, 2014, now U.S. Pat. No. 9,410,051, the entire contents of which are hereby incorporated by reference.

TECHNICAL FIELD

This disclosure relates to certain compounds that could be used for ink compositions, as well as related products and processes.

BACKGROUND

Hot melt inks are a solid at ambient temperature and a liquid at temperatures above ambient temperature. Hot melt inks can be used, for example, in digital printing methods. During printing, the ink is typically heated until it becomes a liquid which is then ejected through a printhead onto a substrate. The ink can solidify on the substrate at ambient temperature.

The hot melt ink can be used with an inkjet printer having heating capabilities, which can eject droplets of ink through tiny nozzles to form small dots, which in turn form an image on a substrate. The resolution of the image printed by the ink is typically measured by the number of dots per inch (DPI).

SUMMARY

This disclosure is based on the unexpected discovery that certain waxes having a relatively low freezing point (e.g., having a freezing point lower than a melting point) can be used to form a hot melt ink composition that forms dots having a relatively large average diameter when the hot melt ink composition is printed on a certain substrate (e.g., a cardboard or a film) without external treatment to the dots.

In one aspect, this disclosure features a hot melt ink composition that includes at least one wax having a freezing point of from about 20° C. to about 50° C. and a melting point of at least about 35° C., and at least one colorant. The composition includes at least about 50 wt % of the at least one wax.

In another aspect, this disclosure features a hot melt ink composition capable of forming dots having an average dot diameter of at least about 15% larger than those formed by Markem-Imaje 5005 TOUCH DRY black ink (Ink 5005) when the dots are formed under the same conditions and without external treatment.

In another aspect, this disclosure features a hot melt ink composition capable of forming dots having an average dot diameter of at least about 85 μm when the composition has a melt viscosity of about 10 cP, each dot is formed by using about 70 picoliter of the composition, and the dots are formed at ambient temperature without external treatment.

In another aspect, this disclosure features a printing process that includes melting any of the hot melt ink compositions described herein in a printhead in an inkjet printer (e.g., a hot melt inkjet printer), and ejecting the hot melt ink composition from the printhead onto a substrate to form an image.

In still another aspect, this disclosure features a product that includes a substrate (e.g., a cardboard or a film) and a solid ink defining an image on the substrate. The solid ink includes any of the hot melt ink compositions described herein.

Embodiments can have one or more of the following features.

The at least one wax has a freezing point of from about 30° C. to about 50° C. (e.g., from about 30° C. to about 40° C.).

The melting point of the at least one wax can be at least about 10° C. (e.g., at least about 15° C.) higher than the freezing point of the at least one wax.

The at least one wax can include an amide alcohol wax, a urethane wax, an ether wax, or an ester wax.

The amide alcohol wax can be stearyl diethanolamide, stearyl isopropanolamide, mono isopropanolamide, or coconut monoisopropanolamide.

The urethane wax can be 2,2,4-trimethylpentane-1,3-diyl bis(stearylcarbamate), or [2-ethyl-2-(octadecylcarbamoyloxymethyl)hexyl]N-octadecylcarbamate.

The ether wax can be polyethylene glycol having a weight average molecular weight of from about 540 g/mol to about 1450 g/mol.

The ester wax can be behenyl erucate, glycerol tribehenate, $C_{32}$-$C_{36}$ branched alkyl stearate, or polyglyceryl-3 stearate.

The hot melt ink composition can include at least about 70 wt % of the at least one wax.

The hot melt ink composition can further include at least one wax having a freezing point higher than 50° C. The at least one wax having a freezing point higher than 50° C. can be 2-(2-(3-octadecylureido)ethoxy)ethyl octadecylcarbamate or octadecyl octadecylcarbamate.

The hot melt ink composition can include at least one tackifier, at least one resin, at least one plasticizer, at least one antioxidant, or at least one dispersant.

The at least one colorant can include a dye or a pigment.

The hot melt ink composition can have a melt viscosity of from about 5 cP to about 25 cP (e.g., from about 10 cP to about 14 cP).

The hot melt ink composition can be substantially free of a polyethylene (e.g., a polyethylene wax).

The hot melt ink composition can consist of: (1) the at least one wax, (2) the at least one colorant, (3) optionally, at least one tackifier, (4) optionally, at least one resin, (5) optionally, at least one plasticizer, (6) optionally, at least one antioxidant, and (7) optionally, at least one dispersant.

The hot melt ink composition can be capable of forming dots having an average dot diameter of at most about 100% larger than those formed by Ink 5005 when the dots are formed under the same conditions and without external treatment.

The hot melt ink composition can be capable of forming dots having an average dot diameter of at most about 120 μm when the composition has a melt viscosity of about 10 cP, each dot is formed by using about 70 picoliter of the composition, and the dots are formed at ambient temperature without external treatment.

Other features and advantages will be apparent from the description and from the claims.

DETAILED DESCRIPTION

In general, this disclosure relates to certain compounds (e.g., a wax) that could be used for an ink composition (e.g., a hot melt ink composition).

In some embodiments, this disclosure relates to a hot melt ink composition that includes at least one wax having a freezing point of from about 20° C. to about 50° C. and a melting point of at least about 35° C., and at least one colorant. The hot melt ink composition can include at least about 50 wt % of the at least one wax. If the wax has more than one freezing point or more than one melting point, at least one of the freezing points is within the range of from about 20° C. to about 50° C. and/or at least one of the melting points is at least about 35° C.

In general, the wax provides the ink composition with the property of being a solid at ambient temperature, but a liquid at an elevated temperature. As mentioned herein, the "ambient temperature" is defined as a temperature from about 20° C. to about 25° C.

In general, the hot melt ink composition should contain enough wax such that the ink composition, as a whole, is a hot melt material. In some embodiments, the ink composition contains at least about 50 wt % (e.g., at least about 55 wt %, at least about 60 wt %, at least about 65 wt %, at least about 70 wt %, at least about 75 wt %, or at least about 80 wt %) and/or at most about 95 wt % (e.g., at most about 90 wt %, at most about 85 wt %, at most about 80 wt %, at most about 75 wt %, or at most about 70 wt %) of the wax. In some embodiments, the hot melt ink composition contains two or more (e.g., three or four) waxes.

In some embodiments, the wax can have a melting point of at least about 35° C. (e.g., at least about 40° C., at least about 45° C., at least about 50° C., at least about 55° C., at least about 60° C., at least about 65° C., at least about 70° C., at least about 75° C., or at least about 80° C.) and/or at most about 150° C. (e.g., at most about 140° C., at most about 130° C., at most about 120° C., at most about 110° C., at most about 100° C., at most about 90° C., or at most about 80° C.). The melting point mentioned herein refers to that measured by Differential Scanning calorimetry. In some embodiments, the wax has a relatively high melting point so that the hot melt ink composition remains as a solid at a relatively high temperature (e.g., about 50° C.) after it is printed on a substrate.

In general, the wax has a freezing point at or above the ambient temperature so that the ink composition can form a solid at ambient temperature after it is printed on a substrate. In some embodiments, the wax can have a freezing point of at least about 20° C. (e.g., at least about 25° C., at least about 30° C., at least about 35° C., or at least about 40° C.) and/or at most about 50° C. (e.g., at most about 45° C., at most about 40° C., at most about 35° C., at most about 30° C., or at most about 25° C.). The freezing point mentioned herein refers to that measured by Differential Scanning calorimetry. In general, the melting and freezing points of the hot melt ink composition can be similar to those of the wax and can have the ranges described above, respectively. Without wishing to be bound by theory, it is believed that the freezing point of the wax should not be too high (e.g., higher than about 50° C.) because a high freezing point can cause the ink composition to freeze rapidly after it is printed on the substrate, thereby reducing drop spread of the melted composition on the substrate and reducing sizes of the dots printed.

In some embodiments, the wax can exhibit thermal hysteresis in melting and freezing points, i.e., having the freezing point lower than the melting point. In some embodiments, the melting point of the wax can be at least about 10° C. (e.g., at last about 15° C., at least about 20° C., at least about 25° C., or at least about 30° C.) higher than the freezing point. Without wishing to be bound by theory, it is believed that, when a hot melt ink composition contains a wax having a freezing point lower than the melting point, the ink composition is capable of forming dots having a relatively large diameter when it is printed on a substrate without any external treatment (e.g., heating after printing, using a high jetting temperature, or pressing the printed dots with a mechanical pressure roller after printing) to the dots formed because the wax takes longer to freeze compared to the wax in a conventional hot melt ink composition. A disadvantage of using an external treatment is that an additional process is required, which requires more labor, hardware, intervention and/or maintenance and therefore increases manufacturing costs.

In some embodiments, the wax can be an amide alcohol wax, a urethane wax, an ether wax, or an ester wax. Exemplary amide alcohol waxes include stearyl diethanolamide, stearyl isopropanolamide, mono isopropanolamide, and coconut monoisopropanolamide. Exemplary urethane waxes include 2,2,4-trimethylpentane-1,3-diyl bis(stearylcarbamate) (i.e., MS 38-48), and [2-ethyl-2-(octadecylcarbamoyloxymethyl)hexyl]N-octadecylcarbamate (i.e., MS 38-37). An exemplary ether wax is a polyethylene glycol having a weight average molecular weight of from about 540 g/mol to about 1450 g/mol (commercially available from Dow Chemical Co, Midland, Mich., under the trade name Carbowax). Exemplary ester waxes include behenyl erucate, glycerol tribehenate, $C_{32}$-$C_{36}$ branched alkyl stearate (e.g., BK-40 commercially available from Koster Keunen, Watertown, Conn.), and polyglyceryl-3 stearate.

In some embodiments, the hot melt ink composition can include one or more waxes (e.g., amide alcohol waxes, urethane waxes, ether waxes, or ester waxes) having a freezing point higher than 50° C. Examples of such waxes include 2-(2-(3-octadecylureido)ethoxy)ethyl octadecylcarbamate (i.e., MS 36-181) and octadecyl octadecylcarbamate (i.e., MS 37-121). In general, the amount of such waxes in the hot melt ink composition is less than the amount of the waxes having a freezing point of from about 20° C. to about 50° C. In some embodiments, the hot melt ink composition can include at most about 50 wt % (e.g., at most about 45 wt %, at most about 40 wt %, at most about 35 wt %, at most about 30 wt %, or at most about 25 wt %) and/or at least about 1 wt % (e.g., at least about 5 wt %, at least about 10 wt %, at least about 15 wt %, at least about 20 wt %, at least about 25 wt %, or at least about 30 wt %) of the waxes having a freezing point higher than 50° C.

In some embodiments, the waxes having a relatively low freezing point (e.g., having a freezing point lower than a melting point) described herein can be compounds of formula (I):

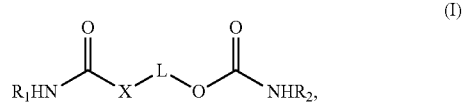

in which each of $R_1$ and $R_2$, independently, is $C_{15}$-$C_{21}$ alkyl; X is O or $NR_3$, in which $R_3$ is H or $C_1$-$C_6$ alkyl optionally substituted with hydroxyl; and L is a $C_3$-$C_{36}$ branched alkylene optionally containing at least one double bond, at least one triple bond, or a $C_3$-$C_{10}$ cycloalkylene group and optionally substituted with $C(O)NH(R_4)$ or $OR_5$, in which $R_4$ is $C_{15}$-$C_{21}$ alkyl and $R_5$ is $C_1$-$C_6$ alkyl or a polyethylene glycol ether group. Any carbon number range mentioned herein includes each individual carbon number within the range. For example, when $C_{15}$-$C_{21}$ alkyl is assigned to $R_1$, $R_1$ can be $C_{15}$ alkyl, $C_{16}$ alkyl, $C_{17}$ alkyl, $C_{18}$ alkyl, $C_{19}$ alkyl, $C_{20}$ alkyl, or $C_{21}$ alkyl. In addition, as used herein, a substituent (e.g., $C(O)NH(R_4)$ or $OR_5$) on the $C_3$-$C_{36}$ branched alkylene is not considered as a part of the branched alkylene. As such, the range $C_3$-$C_{36}$ does not include the number of carbon atoms in the substituent.

The term "alkyl" refers to a monovalent, saturated, linear or branched hydrocarbon moiety, such as —$CH_3$ or —CH($CH_3$)$_2$. The term "alkenylene" refers to a bivalent, linear or branched hydrocarbon moiety, such as —$CH_2$—$CH_2$—$CH_2$—. An example of a branched alkylene is —$CH_2$—CH($CH_3$)—$CH_2$—. The term "cycloalkyl" refers to a monovalent, saturated, cyclic hydrocarbon moiety, such as cyclohexyl. The term "cycloalkylene" refers to a bivalent, saturated, cyclic hydrocarbon moiety, such as

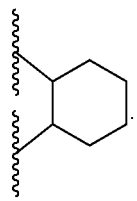 [SMILES: *C1CCCCC1*]

In some embodiments, L can be a $C_4$-$C_{36}$ branched alkylene optionally containing at least one triple bond or a cyclohexylene group and optionally substituted with $C(O)NH(R_4)$ or $OR_5$. For example, L can be —$CH_2$—CH($CH_3$)—, —$CH_2$—$C(CH_3)_2$—CH(CH($CH_3$)$_2$)—, —$CH_2$—$C(CH_3)_2$—$CH_2$—, —$CH_2$—$C(CH_2CH_3)(CH_2CH_2CH_2CH_3)$—$CH_2$—, —$CH_2$—$C(CH_3)(C(O)NH(C_{18}H_{37}))$—$CH_2$—, —$C(CH_3)(CH_2CH_2CH(CH_3)_2)$—C≡C—$C(CH_3)(CH_2CH_2CH(CH_3)_2)$—, or —$CH_2$—$C(CH_2CH_3)(CH_2O(CH_2CH_2O)_nCH_3)$—$CH_2$—, in which n is an integer of 1 to 30.

In some embodiments, a subset of the compounds of formula (I) can be those in which X is O. In such embodiments, L can be —$CH_2$—$C(CH_3)_2$—CH(CH($CH_3$)$_2$)—, —$CH_2$—$C(CH_3)_2$—$CH_2$—, —$CH_2$—$C(CH_2CH_3)(CH_2CH_2CH_2CH_3)$—$CH_2$—, —$CH_2$—$C(CH_3)(C(O)NH(C_{18}H_{37}))$—$CH_2$—, —$C(CH_3)(CH_2CH_2CH(CH_3)_2)$—C≡C—$C(CH_3)(CH_2CH_2CH(CH_3)_2)$—, or —$CH_2$—$C(CH_2CH_3)(CH_2O(CH_2CH_2O)_nCH_3)$—$CH_2$—, in which n is an integer of 1 to 30, and each of $R_1$ and $R_2$ can be $C_{18}H_{37}$.

In some embodiments, another subset of the compounds of formula (I) can be those in which X is $NR_3$. In such embodiments, $R_3$ can be $CH_2$—CH(OH)—$CH_3$, L can be —$CH_2$—CH($CH_3$)—, and each of $R_1$ and $R_2$ can be $C_{18}H_{37}$.

Exemplary compounds of formula (I) include:

(MS 38-48)

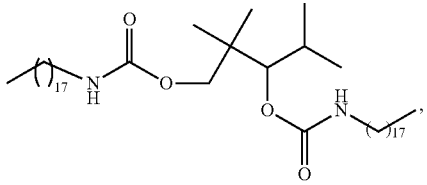

(MS 38-41)

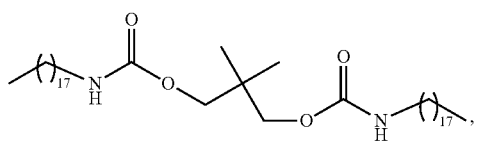

(MS 38-37)

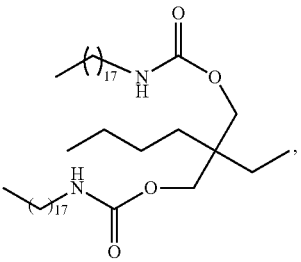

(MS 38-76)

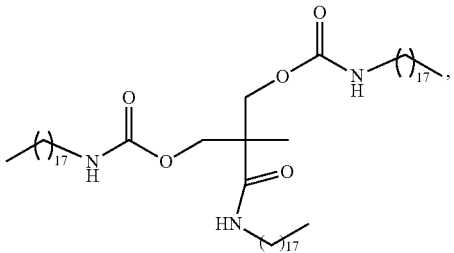

(MS 38-131)

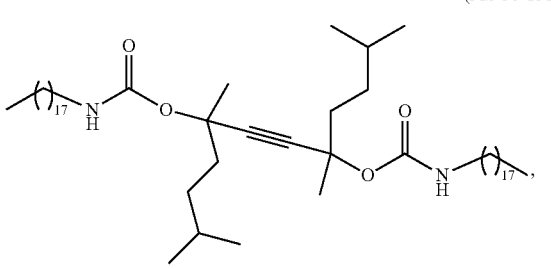

(MS 38-44)

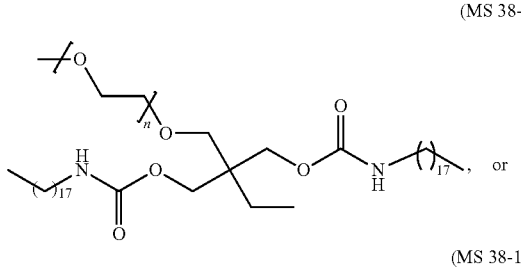

or (MS 38-114)

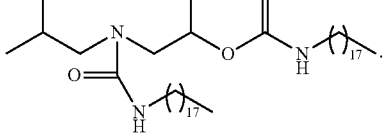

The melting and freezing points of some of certain exemplary waxes (such as compounds of formula (I)) described above are summarized in Table 1 below.

TABLE 1

| Material designation | Melt point (° C.) | Freeze point (° C.) |
|---|---|---|
| MS 36-181 | 113 | 97 |
| MS 37-121 | 83.2 | 71.1 |
| MS 38-48 | 44 | 31 |
| MS 38-37 | 66 | 36 |
| MS 38-41 | 67 | 49 |
| MS 38-76 | 53 | 44, 34 |
| MS 37-131 | 100, 34 | 81, 25 |
| MS 38-44 | 100, 63, 35 | 80, 32, 28 |
| MS 38-114 | 51.2 | 40.2 |
| BK-40 | 38 | 25 |

In general, the waxes described herein can be prepared by methods well known in the art. For example, certain compounds of formula (I) can be made by a diol (or a compound containing both hydroxyl and amino groups) and one or more isocyanates. Scheme 1 below depicts a typical synthetic route for synthesizing exemplary compounds of formula (I):

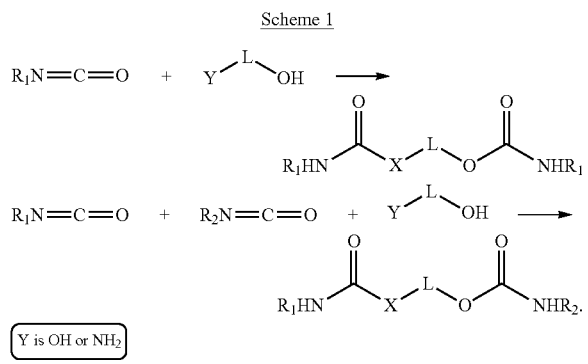

$R_1$, $R_2$, L, and X in Scheme 1 are defined above.

In some embodiments, the waxes described herein (e.g., the compounds of formula (I)) can be incorporated into an ink composition, which can be a hot melt ink composition or a non-hot melt ink composition. When the ink composition is a hot melt ink composition, the ink composition should contain enough wax such that the ink composition, as a whole, is a hot melt material. In some embodiments, the ink composition contains at least about 50 wt % (e.g., at least about 55 wt %, at least about 60 wt %, at least about 65 wt %, at least about 70 wt %, at least about 75 wt %, or at least about 80 wt %) and/or at most about 95 wt % (e.g., at most about 90 wt %, at most about 85 wt %, at most about 80 wt %, at most about 75 wt %, or at most about 70 wt %) of a wax described above. In some embodiments, the ink composition contains two or more (e.g., three or four) of the waxes described above.

In some embodiments, the hot melt ink composition containing one or more of the waxes described herein can be capable of forming dots on a substrate (e.g., a cardboard or a film) that have an average diameter larger than those formed by Ink 5005. Ink 5005 is a hot melt ink composition commercially available from Markem-Imaje Corporation (Keene, N.H.). For example, the dots can have an average diameter of at least about 15% (e.g., at least about 20%, at least about 25%, at least about 30%, at least about 35%, or at least about 40%) and/or at most about 100% (e.g., at most about 50%, at most about 45%, at most about 40%, at most about 35%, or at most about 30%) larger than those formed by Ink 5005 when the dots are formed under the same conditions and without external treatment (such as those described above) to the dots formed. As used herein, the above average dot diameter increase compared to Ink 5005 is also referred to as "dot gain."

In some embodiments, the hot melt ink composition containing one or more of the waxes described herein can be capable of forming dots having an average dot diameter of at least about 85 µm (e.g., at least about 90 µm, at least about 95 µm, at least about 100 µm, at least about 105 µm, or at least about 110 µm) and/or at most about 120 µm (e.g., at most about 115 µm, at most about 110 µm, at most about 105 µm, at most about 100 µm, at most about 95 µm, or at most about 90 µm) when the composition has a melt viscosity of about 10 cP, each dot is formed by using about 70 picoliter of the composition, and the dots are formed at ambient temperature without external treatment (such as those described above) to the dots formed. By contrast, when Ink 5005 is used to form dots under the same conditions, the dots formed generally have an average diameter of at most about 75 µm. In other words, the hot melt ink composition described herein can have an increased dot size (i.e., dot gain) compared to a conventional hot melt ink composition (i.e., Ink 5005).

Without wishing to be bound by theory, it is believed that hot melt ink compositions capable of forming dots that have a relatively large dots size without using any external treatment can have a number of advantages, including improved visual darkness, increased drop spread (i.e., dot gain), and improved barcode validation scores. For example, the dots printed would have relatively large ink coverage to block the background color of the substrate, thereby increasing the visual and machine readable contrast of the image on the substrate. As another example, such a hot melt ink composition can have improved contrast at any given print resolution when compared to commercially available dye-based or pigment-based inks that don't exhibit the dot gain phenomena. As another example, such a hot melt ink composition can reduce the necessary print resolution settings while achieving equivalent darkness, thereby reducing the amount of the ink used and reducing costs. As a further example, by reducing print resolution settings, such a hot melt ink composition can reduce the jetting frequency, which can improve performance such as jet sustainability and reduce maintenance costs by requiring fewer maintenance interventions.

Without wishing to be bound by theory, it is believed that, although a liquid ink composition may be used to print images on a substrate with a relatively large dot size, a hot melt ink composition can possess advantages compared to a liquid ink composition. For example, a liquid ink composition is a liquid at room temperature, typically oil based, and is capable of diffusing into the surface of the substrate, causing the images printed to diffuse into the substrate, resulting in blurred lines or low quality images. By contrast, a hot melt ink composition is a solid at room temperature and is typically not diffused into the surface of the substrate, which can result in images with higher qualities (such as better relative line width and edge definition).

In general, the hot melt ink composition described herein can include at least one colorant, such as a dye or a pigment. The dye or pigment can be either an organic or inorganic material. Examples of dyes include anthraquinone and peri-none reds such as solvent red 172, solvent red 111, solvent red 222, solvent red 207, and solvent red 135; anthraquinone blues such as solvent blue 104, solvent violet 13; anthraquinone greens such as solvent green 3 and solvent green 5; xanthane, quinoline, quinophthalone, pyrazolone, methine, and anthraquinoid yellows such as solvent yellow 98, solvent yellow 33, disperse yellow 54, solvent yellow 93, disperse yellow 82, and solvent yellow 163. Examples of pigments include pigment blues (PB) 15, 15:3, 15:4, 16, 22, 28, 64, 68; pigment reds (PR) 3, 4, 48, 81, 97, 113, 122, 175, 202, 217; pigment yellows (PY) 2, 7, 53, 111, 155, 151, 175, 194; pigment blacks 7, carbon black, graphite; and pigment white titanium dioxide. Other exemplary dyes or pigments have been described in, e.g., U.S. Pat. Nos. 6,702,884, 5,863,319, and 5,891,228. In some embodiments, the hot melt ink composition can include at least about 1 wt % (e.g., at least about 5 wt %, at least about 10 wt %, or at least about 15 wt %) and at most about 25 wt % (e.g., at most about 20 wt %, at most about 15 wt %, at most about 10 wt %, or at most about 5 wt %) of the colorant.

In some embodiments, the hot melt ink composition described herein can further include at least one tackifier, at least one resin, at least one plasticizer, at least one antioxidant, and/or at least one dispersant.

In some embodiments, the hot melt ink composition described herein can optionally include one or more tackifiers. In general, a tackifier can improve adhesion between the ink composition and a substrate (e.g., a cardboard or a film). Examples of tackifiers include glycerol esters, pentaerythritol esters, hydrocarbons, rosin, rosin esters, modified rosin esters (e.g., hydrogenated, acid, or phenolic-modified rosin esters), cumarone-indene polymers, cyclic ketone polymers, styrene allyl alcohol polymers, polystyrenes, polyvinyl toluene/methylstyrene polymers, polyvinyl chloride, polyvinyl alcohol, ethylene/vinyl acetate, ethylene/acrylic acid, alkyl hydrocarbon polymers, aryl hydrocarbon polymers, alkyl aryl hydrocarbon polymers, terpene polymers, ethylene carbon monoxide copolymers, vinyl chloride/vinyl alcohol copolymers, polyvinyl butyral, polyketones, styrene/acrylic copolymers, polybutenes, polybutadienes, styrene-isoprene-styrene, styrene-butadiene-styrene, polyvinyl pyrrolidone, polyvinyl pyridine, vinyl pyrrolidone/vinyl acetate, polyurethanes, polyesters, polyamides, cellulose esters, cellulose ethers, polyols, styrene-acrylates, polypropylene, chlorinated polypropylene, chlorinated paraffin, gilsonite and other asphaltic materials, cyclic hydrocarbon polymer, halogenated polymers, acrylics, epoxides, novolacs, and other synthetic and natural resins. A commercially available tackifier is polyterpene available from Goodyear under the trade name Wingtack 86. In some embodiments, the ink composition contains at least about 1 wt % (e.g., at least about 5 wt %, at least about 10 wt %, or at least about 15 wt %) and at most about 25 wt % (e.g., at most about 20 wt %, at most about 15 wt %, at most about 10 wt %, or at most about 5 wt %) of the tackifier.

In some embodiments, the hot melt ink composition described herein can optionally include one or more resins. The resin can provide the ink composition with a desired viscosity, thermal stability, flexibility, and adhesion properties. Examples of resins include acacia (gum arabic); gum ghatti; guar gum; locust (carob) bean gum; karaya gum (sterculia gum); gum tragacanth; chicle; highly stabilized rosin ester; tall oil; manila copais; corn gluten; coumarone-indene resins; crown gum; damar gum; p, alpha-dimethylstyrene; gum elemi; ethylene oxide polymer and its adducts; ethylene oxide/propylene oxide copolymer and its adducts; galbanum resin; gellan gum; ghatti gum; gluten gum; gualac gum; guarana gum; heptyl paraben; cellulose resins, including methyl and hydroxypropyl; hydroxypropyl methylcellulose resins; isobutylene-isoprene copolymer; mastic gum; oat gum; opopanax gum; polyacrylamide; modified polyacrylamide resin; polylimonene; polyisobutylene; polymaleic acid; polyoxyethylene derivatives; polypropylene glycol; polyvinyl acetate; polyvinyl alcohol; polyvinyl polypyrrolidone; polyvinyl pyrrolidone; rosin, adduct with fumaric acid, pentaerythritol ester; rosin, gum, glycerol ester; rosin, gum or wood, pentaerythritol ester; rosin, gum or wood, partially hydrogenated, glycerol ester; rosin, gum or wood, partially hydrogenated, pentaerythritol ester; rosin, methyl ester, partially hydrogenated; rosin, partially dimerized, glycerol ester; rosin, partially hydrogenated; rosin and rosin derivatives; rosin, polymerized, glycerol ester; rosin, tall oil, glycerol ester; rosin, wood; rosin, wood, glycerol ester; purified shellac; styrene; styrene terpolymers; styrene copolymers; sucrose acetate isobutyrate; terpene resins, natural and synthetic; turpentine gum; vinylacetate; vinyl chloride-vinylidene chloride copolymer; zanthan gum; and zein.

In general, the hot melt ink composition includes enough resin to achieve the desired viscosity, stability, flexibility, and adhesion. In some embodiments, the ink composition contains at least about 1 wt % (e.g., at least about 5 wt %, at least about 10 wt %, or at least about 15 wt %) and at most about 25 wt % (e.g., at most about 20 wt %, at most about 15 wt %, at most about 10 wt %, or at most about 5 wt %) of the resin. In some embodiments, the ink composition contains no resin.

In some embodiments, the hot melt ink composition described herein can optionally include one or more plasticizers. In general, a plasticizer can reduce the viscosity and increase flexibility of the ink composition. Examples of plasticizers include aromatic sulfonamides, phthalates, acetates, adipates, amides, azelates, epoxides, glutarates, laurates, oleates, sebacates, stearates, sulfonates, tallates, phosphates, benzoin ethers, and trimellitates. In some embodiments, the ink composition contains at least about 1 wt % (e.g., at least about 2 wt %, at least about 4 wt %, at least about 6 wt %, or at least about 8 wt %) and at most about 10 wt % (e.g., at most about 9 wt %, at most about 7 wt %, at most about 5 wt %, or at most about 3 wt %) of the plasticizer.

In some embodiments, the hot melt ink composition described herein can optionally include one or more antioxidants. In general, an antioxidant can inhibit oxidation (e.g., thermally induced oxidation) of the ink composition (e.g., when the ink composition is in a hot molten state during jetting). Examples of antioxidants include butylated hydroxyanisole (BHA); butylated hydoxytoluene (BHT); propyl gallate; tert-butyl hydroquinone (TBHQ); ethylenediaminetetraacetic acid (EDTA); methyl paraben; and propyl paraben. A commercial example of the antioxidant is Irganox 1010 (i.e., a hindered phenol) available from BASF Corporation (Florham Park, N.J.). In some embodiments, the ink composition contains at least about 0.1 wt % (e.g., at least about 0.5 wt %, at least about 1 wt %, or at least about 3 wt %) and at most about 5 wt % (e.g., at most about 4 wt %, at most about 3 wt %, at most about 2 wt %, or at most about 1 wt %) of the antioxidant.

In some embodiments, the hot melt ink composition described herein can optionally include one or more dispersants. In general, a dispersant can assist in stabilizing an insoluble component (e.g., a colorant) in the hot melt ink composition. For example, the dispersant can prevent agglomeration of a colorant (e.g., a pigment) in the ink composition. Examples of dispersants include Solsperse 13,650, 13,940, 17,000, J910; Byk 108; Tego Dispers 700; UNIQEMA 5543; and EFKA 5244, 5207, 6750; which are all commercially available from Lubrizol; Byk Chemie; Tego Chemie; Croda; and BASF, respectively. In some embodiments, the ink composition contains at least about 1 wt % (e.g., at least about 2 wt %, at least about 4 wt %, at least about 6 wt %, or at least about 8 wt %) and at most about 10 wt % (e.g., at most about 9 wt %, at most about 7 wt %, at most about 5 wt %, or at most about 3 wt %) of the dispersant.

In general, the hot melt ink composition can have any suitable melt viscosity. As mentioned herein, the term "melt viscosity" refers to the shear viscosity of an ink composition in its molten state. In some embodiments, the ink composition can have a melt viscosity of at least about 5 centiPoise (cP) (e.g., at least about 10 cP, at least about 15 cP, or at least about 20 cP) and/or at most about 25 cP (e.g., at most about 20 cP, at most about 15 cP, or at most about 10 cP) measured at 125° C. For example, the ink composition can have a melt viscosity from about 10 cP to about 14 cP measured at 125° C.

In some embodiments, the hot melt ink composition is substantially free of a certain material. For example, the hot melt ink composition can be substantially free of a polyethylene (e.g., a polyethylene wax).

The hot melt ink composition described herein can be used with a drop-on-demand inkjet printer (e.g., a hot melt piezo inkjet printer). An example of a commercial drop-on-demand inkjet printer is a Markem-Imaje model 5200 inkjet printer.

In some embodiments, the hot melt ink composition described herein can be used in a printing process that includes melting the hot melt ink composition in a printhead in an inkjet printer, and ejecting the hot melt ink composition from the printhead onto a substrate to form an image.

This disclosure also features a product that includes a substrate and a solid ink defining an image on the substrate, in which the solid ink includes the hot melt ink composition described herein. The substrate can be any suitable materials (e.g., porous or non-porous materials), such as films, coated papers, plastics, metals, and cardboards. In some embodiments, the substrate can be a package material, such as a cardboard (e.g., a corrugated cardboard) or a film (e.g., a shrink wrap).

While the waxes has been described as suitable for use in ink compositions, in some embodiments, the waxes described herein can also be used in other applications. For example, the waxes described herein can be used as polish waxes, viscosity modifiers (e.g., pressure sensitive adhesives), or rheology modifiers (e.g., in hot melt materials). As another example, the waxes described herein can be used in gaskets (e.g., toilet bowl gaskets) or protective covering for surfaces.

The contents of all publications cited herein (e.g., patents, patent application publications, and articles) are hereby incorporated by reference in their entirety.

The following examples are illustrative and not intended to be limiting.

Examples 1-6 and Comparative Example 1

Certain waxes (i.e., MS 38-48, MS 37-121, and MS 36-181) used in Examples 1-6 were prepared by the method described in Example 7 below. The reactants and the waxes produced are summarized in Table 2 below.

TABLE 2

| Reactant 1 | Reactant 2 | Resulting wax material |
|---|---|---|
| stearyl isocyanate | 2,2,4-trimethylpentane-1,3-diol | MS 38-48 |
| stearyl isocyanate | stearyl alcohol | MS 37-121 |
| stearyl isocyanate | 2-(2-aminoethoxy)ethan-1-ol | MS 36-181 |

BK-40 and PELEMOL GTB used in Examples 1-6 were purchased from Koster Keunen, Watertown, Conn. and Phoenix Chemical, Somerville, N.J., respectively.

The colorant dispersions used in Examples 1-6 were manufactured by mixing a wax medium, a suitable dispersant, and a pigment such that an ink jet quality dispersion was achieved, as determined by particle size. After the ingredients were melted and pre-mixed, the particle size of the pigment was reduced utilizing a bead mill.

The wax materials and the colorant dispersions were then mixed to form the inks of Examples 1-6. The compositions of the inks of Examples 1-6 are summarized in Table 3 below.

TABLE 3

| Example # | Wax #1 | Wax #1 (wt %) | Wax #2 | Wax #2 (wt %) | Colorant dispersion | Colorant (wt %) |
|---|---|---|---|---|---|---|
| Example 1 | MS 38-48 | 85 | None | N/A | GT09-34 | 15 |
| Example 2 | MS 38-48 | 17.5 | BK-40 | 57.5 | GT09-34 | 25 |
| Example 3 | MS 38-48 | 67.37 | BK-40 | 11.58 | GT09-47 | 21.05 |
| Example 4 | MS 38-48 | 55 | MS 37-121 | 20 | GT09-34 | 25 |
| Example 5 | BK-40 | 50 | MS 36-181 | 25 | GT09-34 | 25 |
| Example 6 | MS 38-48 | 66.67 | PELEMOL GTB | 11.46 | GT09-34 | 20.83 |
| Comparative Example 1 | Markem-Imaje 5005 TOUCH DRY Black Ink | | | | | |

In Table 1, MS 38-48 is 2,2,4-trimethylpentane-1,3-diyl bis(stearylcarbamate); MS 37-121 is octadecyl octadecylcarbamate; MS 36-181 is 2-(2-(3-octadecylureido)ethoxy) ethyl octadecylcarbamate; BK-40 is a $C_{32}$-$C_{36}$ branched alkyl stearate; PELEMOL GTB is a glycerol tribehenate; GT09-34 is a mixture containing MS37-121 (50 wt %), Irganox 1010 (2 wt %), Solsperse J910 (Lubrizol Limited, Cleveland, Ohio) (16 wt %), and Special Black 4A (Evonik Corporation, Theodore, Ala.) (32 wt %); GT09-47 is a mixture containing MS 38-48 (50 wt %), Irganox 1010 (2 wt %), Solsperse J910 (16 wt %), and Special Black 4A (32 wt %).

The properties of the inks in Examples 1-6 and Comparative Example 1 were tested using the following methods:

Melting and freezing points are obtained using a Perkin Elmer Pyris 7e DSC using the programmed run sequence summarized in Table 4:

TABLE 4

| Step # | Starting Temperature (° C.) | Ending Temperature (° C.) | Ramp Rate (° C.) |
|---|---|---|---|
| 1 | 0 | 140 | 50/minute |
| 2 | 140 | 0 | 50/minute |
| 3 | 0 | 0 | 0/1 minute |
| 4 | 0 | 140 | 20/minute |
| 5 | 140 | 0 | 20/minute |

Melting point values taken were the peak heights found during the second melt and freeze cycle.

Melt viscosity was measured by using a Brookfield viscometer (Model DVII) with an attached thermal cell. 8.0 grams of an ink was heated in the ink cup to melt the ink. A #18 spindle running at 60 RPM was used to take viscosity measurement after shearing for 10 minutes minimum.

Dot gain measurements are measured by utilizing an Olympus SZX12 microscope, with Olympus Stream Essentials software, version 1.9. Microphotographs were taken after calibration. The resulting drop diameters were measured with the software accompanying the microscope, and contrasted to the comparative example.

The results are summarized in Table 5 below.

TABLE 5

| Example # | Viscosity (cP) | Melt Point (° C.) | Freezing Point (° C.) | Dot Gain |
|---|---|---|---|---|
| Example 1 | 12.8 | 43 | 32 | 15% |
| Example 2 | 10.1 | 36, 66 | 21.6, 52 | 53% |
| Example 3 | 12.9 | 41 | 32 | 30% |
| Example 4 | 12.6 | 43, 75 | 30, 57 | 21% |
| Example 5 | 11.5 | 38 | 23 | 24% |
| Example 6 | 13.9 | 42 | 33 | 30% |
| Comparative Example 1 | 9 | 58 | 51 | Control |

The dot gain values in Table 2 are the percentage increases of the dot diameters obtained from inks in Examples 1-6 compared to the dot diameter obtained from the ink in Comparative Example 1. These dot gains are average values obtained from 7 to 10 measurements.

Example 7: Synthesis of MS38-48

29.55 grams (0.1 moles) of stearyl isocyanate (Mol. Weight: 295.50) was added to a 100 ml beaker and placed onto a Mantle Minder. The isocyanate was then heated to approximately 80° C. While monitoring temperature, a stoichiometric amount (0.2 moles) of 2,2,4-trimethylpentane-1,3 diol (TMPD) was added to the beaker while the solution was mixed by using a magnetic stir bar. TMPD was added at an addition rate such that the temperature of the solution in the beaker did not rise above 120° C. Once all TMPD was added, the reaction was monitored via FTIR based on the isocyanate peak found around 2263 cm$^{-1}$. Once the peak at 2263 cm$^{-1}$ reached baseline, the reaction was considered complete. The product thus obtained (i.e., MS38-48) was evaluated for its properties without further purification. The melting and freezing points of the product are summarized in Table 1 above.

Example 8: Synthesis of MS 38-41, MS 38-37, MS 38-76, MS 38-44, MS 38-114, MS 37-131, MS 37-121, and MS 36-181

MS 38-41, MS 38-37, MS 38-76, MS 38-44, MS 38-114, MS 37-131, MS 37-121, and MS 36-181 were synthesized in a manner similar to MS 38-48 by using appropriate starting materials. The melting and freezing points of these materials are summarized in Table 1 above.

Other embodiments are within the scope of the following claims.

What is claimed is:

1. A compound of formula (I):

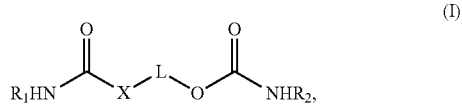

(I)

wherein
each of $R_1$ and $R_2$, independently, is $C_{15}$-$C_{21}$ alkyl;
X is O; and
L is (a) a $C_6$-$C_{36}$ branched alkylene optionally containing at least one double bond, at least one triple bond, or a $C_3$-$C_{10}$ cycloalkylene group and optionally substituted with C(O)NH($R_4$) or O$R_5$, (b) a $C_3$-$C_{36}$ branched alkylene containing at least one double bond, at least one triple bond, or a $C_3$-$C_{10}$ cycloalkylene group and optionally substituted with C(O)NH ($R_4$) or O$R_5$, or (c) a $C_3$-$C_{36}$ branched alkylene substituted with C(O)NH($R_4$) or O$R_5$, the a $C_3$-$C_{36}$ branched alkylene optionally containing at least one double bond, at least one triple bond, or a $C_3$-$C_{10}$ cycloalkylene group, in which $R_4$ is $C_{15}$-$C_{21}$ alkyl and $R_5$ is $C_1$-$C_6$ alkyl or a polyethylene glycol ether group.

2. The compound of claim 1, wherein L is a $C_6$-$C_{36}$ branched alkylene optionally containing at least one triple bond and optionally substituted with C(O)NH($R_4$) or O$R_5$, or a $C_3$-$C_{36}$ branched alkylene substituted with C(O)NH($R_4$) or O$R_5$.

3. The compound of claim 2, wherein L is —CH$_2$—C(CH$_3$)$_2$—CH(CH(CH$_3$)$_2$)—, —CH$_2$—C(CH$_2$CH$_3$)(CH$_2$CH$_2$CH$_2$CH$_3$)—CH$_2$—, —CH$_2$—C(CH$_3$)(C(O)NH(C$_{18}$H$_{37}$))—CH$_2$—, —C(CH$_3$)(CH$_2$CH$_2$CH(CH$_3$)$_2$)—C≡C—C(CH$_3$)(CH$_2$CH$_2$CH(CH$_3$)$_2$)—, or —CH$_2$—C(CH$_2$CH$_3$)(CH$_2$O(CH$_2$CH$_2$O)$_n$CH$_3$)—CH$_2$—, in which n is an integer of 1 to 30.

4. The compound of claim 3, wherein each of $R_1$ and $R_2$ is $C_{18}$H$_{37}$.

5. The compound of claim 4, wherein the compound is

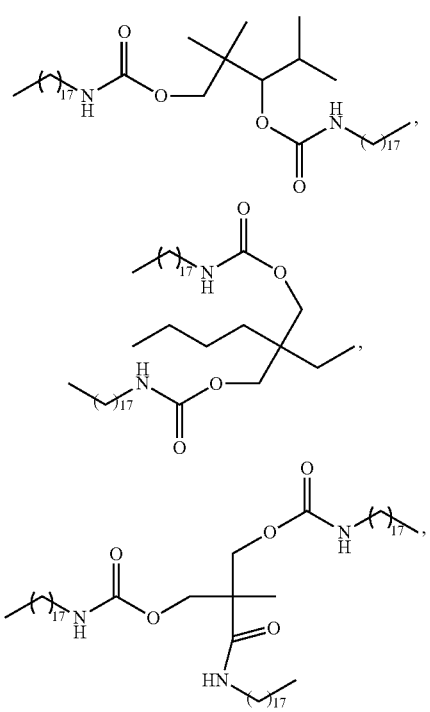

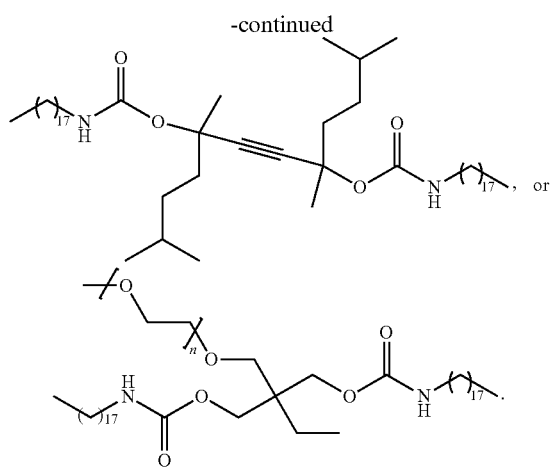

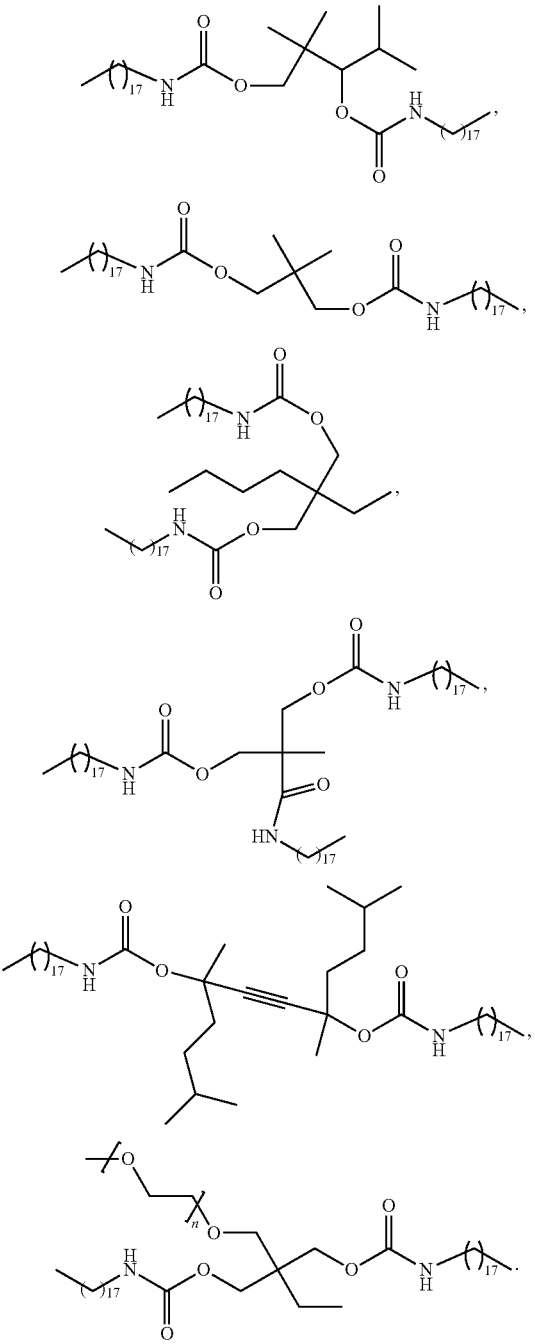

6. An ink composition, comprising at least one compound of formula (I):

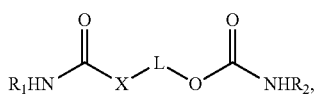

wherein each of $R_1$ and $R_2$, independently, is a $C_{15}$-$C_{21}$ alkyl; X is O or $NR_3$, in which $R_3$ is H or $C_1$-$C_6$ alkyl optionally substituted with hydroxyl; and L is a $C_3$-$C_{36}$ branched alkylene optionally containing at least one double bond, at least one triple bond, or a $C_3$-$C_{10}$ cycloalkylene group and optionally substituted with $C(O)NH(R_4)$ or $OR_5$, in which $R_4$ is a $C_{15}$-$C_{21}$ alkyl and $R_5$ is a $C_1$-$C_6$ alkyl or a polyethylene glycol ether group; and at least one colorant.

7. The composition of claim 6, wherein the composition comprises at least about 50 wt % of the at least one compound of formula (I).

8. The composition of claim 6, further comprises at least one tackifier, at least one resin, at least one plasticizer, at least one antioxidant, or at least one dispersant.

9. The composition of claim 6, wherein the composition is a hot melt ink composition.

10. The composition of claim 9, wherein the composition has a melt viscosity of from about 5 cP to about 25 cP measured at 125° C.

11. The composition of claim 6, wherein X is O.

12. The composition of claim 11, wherein L is a $C_4$-$C_{36}$ branched alkylene optionally containing at least one triple bond and optionally substituted with $C(O)NH(R_4)$ or $OR_5$.

13. The composition of claim 12, wherein L is —$CH_2$—$C(CH_3)_2$—$CH(CH(CH_3)_2)$—, —$CH_2$—$C(CH_3)_2$—$CH_2$—, —$CH_2$—$C(CH_2CH_3)(CH_2CH_2CH_2CH_3)$—$CH_2$—, —$CH_2$—$C(CH_3)(C(O)NH(C_{18}H_{37}))$—$CH_2$—, —$C(CH_3)(CH_2CH_2CH(CH_3)_2)$—$C\equiv C$—$C(CH_3)(CH_2CH_2CH(CH_3)_2)$—, or —$CH_2$—$C(CH_2CH_3)(CH_2O(CH_2CH_2O)_nCH_3)$—$CH_2$—, in which n is an integer of 1 to 30.

14. The composition of claim 13, wherein each of $R_1$ and $R_2$ is $C_{18}H_{37}$.

15. The composition of claim 14, wherein the compound is

16. The composition of claim 6, wherein X is $NR_3$, in which $R_3$ is $CH_2$—$CH(OH)$—$CH_3$.

17. The composition of claim 16, wherein L is a $C_4$-$C_{36}$ branched alkylene optionally containing at least one triple bond and optionally substituted with $C(O)NH(R_4)$ or $OR_5$.

18. The composition of claim 17, wherein L is —$CH_2$—$CH(CH_3)$—.

19. The composition of claim 18, wherein each of $R_1$ and $R_2$ is $C_{18}H_{37}$.

20. The composition of claim 19, wherein the compound is

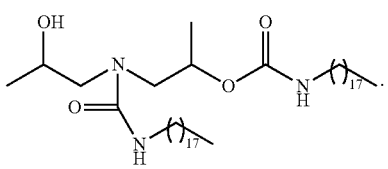

21. A printing process, comprising:
melting the hot melt ink composition of claim 9 in a printhead in an inkjet printer, and ejecting the hot melt ink composition from the printhead onto a substrate to form an image.

22. A compound of formula (I):

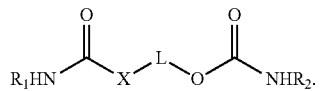

(I)

wherein each of $R_1$ and $R_2$, independently, is $C_{15}$-$C_{21}$ alkyl; X is $NR_3$, in which $R_3$ is H or $C_1$-$C_6$ alkyl optionally substituted with hydroxyl; and L is a $C_3$-$C_{36}$ branched alkylene optionally containing at least one double bond, at least one triple bond, or a $C_3$-$C_{10}$ cycloalkylene group and optionally substituted with $C(O)NH(R_4)$ or $OR_5$, in which $R_4$ is $C_{15}$-$C_{21}$ alkyl and $R_5$ is $C_1$-$C_6$ alkyl or a polyethylene glycol ether group.

23. The compound of claim 22, wherein X is $NR_3$, in which $R_3$ is $CH_2$—CH(OH)—$CH_3$.

24. The compound of claim 23, wherein L is a $C_4$-$C_{36}$ branched alkylene optionally containing at least one triple bond and optionally substituted with $C(O)NH(R_4)$ or $OR_5$.

25. The compound of claim 24, wherein L is —$CH_2$—$CH(CH_3)$—.

26. The compound of claim 25, wherein each of $R_1$ and $R_2$ is $C_{18}H_{37}$.

27. The compound of claim 26, wherein the compound is

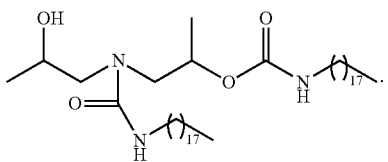

\* \* \* \* \*

UNITED STATES PATENT AND TRADEMARK OFFICE
CERTIFICATE OF CORRECTION

PATENT NO. : 9,944,806 B2
APPLICATION NO. : 14/713683
DATED : April 17, 2018
INVENTOR(S) : Richard C. Woudenberg and Michael P. Secord Page 1 of 1

It is certified that error appears in the above-identified patent and that said Letters Patent is hereby corrected as shown below:

In the Claims

Column 14, Line 15, in Claim 1, delete "the a" and insert -- a -- therefor.

Column 17, Lines 17-20, in Claim 22, delete " 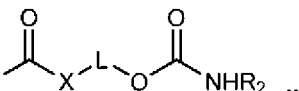 ."

and insert -- 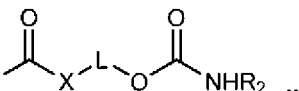, -- therefor.

Signed and Sealed this
Twenty-ninth Day of May, 2018

Andrei Iancu
*Director of the United States Patent and Trademark Office*